US010175382B2

(12) United States Patent
Radley et al.

(10) Patent No.: US 10,175,382 B2
(45) Date of Patent: *Jan. 8, 2019

(54) IDENTIFICATION OF MATERIALS

(71) Applicant: Kromek Limited, Sedgefield (GB)

(72) Inventors: Ian Radley, Sedgefield (GB); Benjamin John Cantwell, Sedgefield (GB); Andrew Keith Powell, Sedgefield (GB)

(73) Assignee: Kromek Limited, Sedgefield (GB)

( * ) Notice: Subject to any disclaimer, the term of this patent is extended or adjusted under 35 U.S.C. 154(b) by 175 days.

This patent is subject to a terminal disclaimer.

(21) Appl. No.: 14/441,929

(22) PCT Filed: Nov. 11, 2013

(86) PCT No.: PCT/GB2013/052955
§ 371 (c)(1),
(2) Date: May 11, 2015

(87) PCT Pub. No.: WO2014/076461
PCT Pub. Date: May 22, 2014

(65) Prior Publication Data
US 2015/0285941 A1    Oct. 8, 2015

(30) Foreign Application Priority Data
Nov. 13, 2012 (GB) .................................. 1220418.6

(51) Int. Cl.
*G01N 23/083* (2018.01)
*G01V 5/00* (2006.01)
*G01N 23/087* (2018.01)

(52) U.S. Cl.
CPC ......... *G01V 5/0041* (2013.01); *G01N 23/083* (2013.01); *G01N 23/087* (2013.01); *G01V 5/0016* (2013.01)

(58) Field of Classification Search
CPC ........... G01N 23/087; G01N 23/20083; G01N 23/083; G01V 5/00
See application file for complete search history.

(56) References Cited

U.S. PATENT DOCUMENTS 3,809,904 A * 5/1974 Clarke ............. G01N 23/20083
250/307
4,149,081 A   4/1979 Seppi
(Continued)

FOREIGN PATENT DOCUMENTS

GB    2285506 A    7/1995
JP    S53134387 A  11/1978
(Continued)

OTHER PUBLICATIONS

Savage, John, "International Search Report" prepared for PCT/GB2013/052955, dated Jan. 20, 2014, three pages.
(Continued)

*Primary Examiner* — Wyatt Stoffa
*Assistant Examiner* — Hsien Tsai
(74) *Attorney, Agent, or Firm* — Winstead PC

(57) ABSTRACT

A method of radiological examination of an object for the identification and detection of the composition the object comprising the steps of: irradiating an object under test with high energy radiation such as x-rays or gamma-rays and collecting radiation emergent from the object at a suitable detector system in such manner that emergent radiation intensity data is collected for the entire volume of the object under test; numerically processing the radiation intensity data to obtain a first data item correlated to the total number of electrons within the sample; applying an alternative method to obtain a second data item correlated to another property of the sample; using the first and second data items to derive an indication of the material content of the sample.

18 Claims, 1 Drawing Sheet

(56) References Cited

U.S. PATENT DOCUMENTS

| | | | | |
|---|---|---|---|---|
| 4,571,491 | A | * | 2/1986 | Vinegar ............... G01N 23/083 250/252.1 |
| 5,930,326 | A | * | 7/1999 | Rothschild ............. G01N 23/04 378/57 |
| 7,286,638 | B2 | | 10/2007 | Ledoux et al. |
| 7,697,657 | B2 | * | 4/2010 | Walter ................. A61B 6/4241 378/4 |
| 8,781,072 | B2 | * | 7/2014 | Robinson ............. G01N 23/087 378/88 |
| 9,784,697 | B2 | * | 10/2017 | Ha ........................ G01N 23/20 |
| 2001/0004395 | A1 | * | 6/2001 | McCrory ........... A61K 49/0409 378/162 |
| 2002/0044628 | A1 | * | 4/2002 | Hussein ............... G01B 15/025 378/89 |
| 2003/0231739 | A1 | * | 12/2003 | Rosner ................. G01N 23/046 378/57 |
| 2006/0078085 | A1 | * | 4/2006 | Zanker ................. G01N 23/046 378/57 |
| 2008/0008292 | A1 | * | 1/2008 | Krmar .................... A61B 6/482 378/89 |
| 2008/0205583 | A1 | * | 8/2008 | Seppi ..................... G01N 23/04 378/9 |
| 2008/0240356 | A1 | * | 10/2008 | Robinson ............. G01V 5/0058 378/98.2 |
| 2008/0283761 | A1 | * | 11/2008 | Robinson ............... G01N 23/04 250/370.09 |
| 2009/0129544 | A1 | | 5/2009 | Chen et al. |
| 2011/0305318 | A1 | * | 12/2011 | Robinson ............. G01N 23/087 378/88 |
| 2013/0285657 | A1 | | 10/2013 | Espy et al. |
| 2014/0241505 | A1 | * | 8/2014 | Xu ................... G01N 23/20066 378/87 |

FOREIGN PATENT DOCUMENTS

| | | |
|---|---|---|
| JP | H10318951 A | 12/1998 |
| JP | 2004108994 A | 4/2004 |
| JP | 2007082663 A | 4/2007 |
| JP | 20098441 A | 1/2009 |
| JP | 200942134 A | 2/2009 |
| JP | 200953090 A | 3/2009 |
| JP | 2009515190 A | 4/2009 |
| JP | 2009122043 A | 6/2009 |
| JP | 2009122108 A | 6/2009 |
| WO | WO-9802763 A1 | 1/1998 |
| WO | WO2007056420 A2 | 5/2007 |
| WO | WO-2011094686 A2 | 8/2011 |
| WO | WO-2014076462 A2 | 5/2014 |

OTHER PUBLICATIONS

Anderson, A.C., et al.; "Self-Diffusion Coefficient and Nuclear Susceptibility of Liquid He$^3$"; Physical Review Letters, vol. 5, No. 4; Aug. 15, 1960; pp. 133-135.

De Deene, Yves, et al.; "Three Dimensional Radiation in Lung-Equivalent Regions by use of a Radiation Sensitive Gel Foam: Proof of Principle"; Medical Physics, vol. 33, No. 7; Jun. 26, 2006; pp. 2586-2597.

* cited by examiner

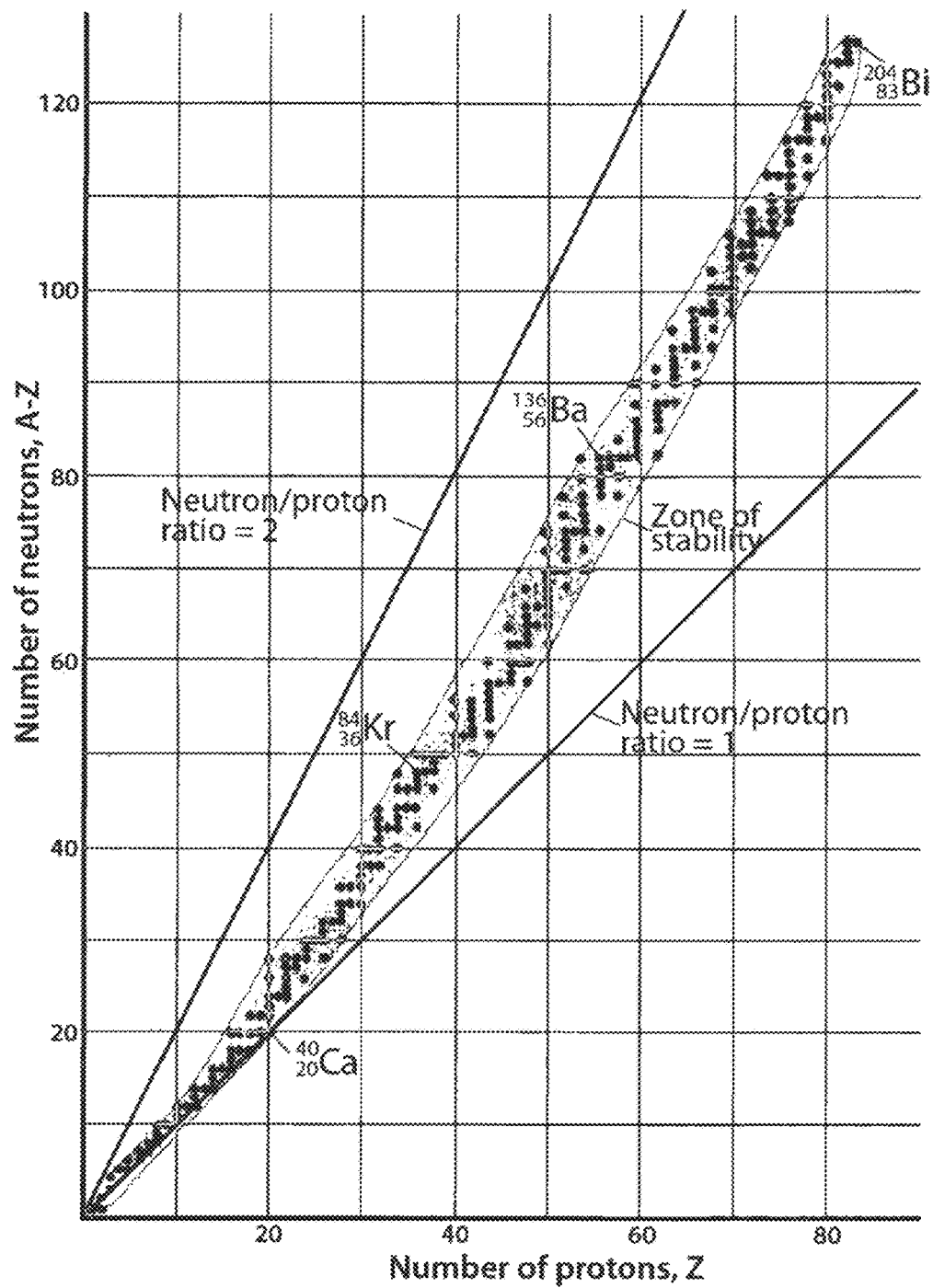

IDENTIFICATION OF MATERIALS

Summary

The invention relates to a method for the identification of materials using high energy radiation such as X-rays or gamma-rays and in particular uses an X-ray all-atom technique in conjunction with one or more all-atom techniques.

Brief Description of the Drawing

FIG. 1 is a standard graph of stable isotopes.

Detailed Description

The invention particularly relates to an apparatus and method making use of high energy radiation such as x-rays or gamma-rays to scan objects where it is desirable to gain information about the internal contents and/or composition of the contained material.

Traditional dual-energy techniques use the density of a liquid for identification. In order to calculate the density, information about the size of the sample under investigation is required. This can be very difficult to calculate for complex 3 dimensional structures, such as numerous bottles in bags.

In accordance with the invention in a first aspect, a method of radiological examination of an object for the identification and detection of the composition the object comprises the steps of:
irradiating an object under test with high energy radiation such as x-rays or gamma-rays and collecting radiation emergent from the object at a suitable detector system in such manner that emergent radiation intensity data is collected for the entire volume of the object under test;
numerically processing the radiation intensity data to obtain a first data item correlated to the total number of electrons within the sample;
applying an alternative method to obtain a second data item correlated to another property of the sample;
using the first and second data items to derive an indication of the material content of the sample.

This invention removes the requirement to measure the sample by using a radiological measurement together with another orthogonal technology. The radiological technique is used to derive a first data item correlated to the total number of electrons within the sample. An orthogonal technology is used to generate an orthogonal second data item correlated in some other way to a property of the sample and in particular preferably correlated in some other way to the all atom properties of the sample. The first and second data items may then be used, and for example co-processed numerically, to derive an indication of the material content of the sample without the need for a measurement of the volume.

The key to the invention lies in the use of the radiological measurement to obtain a data item correlated to the total number of electrons within the object in conjunction with a further measurement of some other property of the sample which can be co-processed with this measurement of the total number of electrons to draw inferences about the material content without requiring measurement of the volume. Any second property of the sample that meets this criterion could be considered.

Conveniently for example a second property of the sample is one that can be processed numerically with the first data item correlated to the total number of electrons within the object so that the respective volume contributions to the data items can be cancelled out. Conveniently both data items are derived as total numbers integrated over the volume under investigation, so that knowledge of the volume of the sample is no longer required. Conveniently for example the second property of the sample is correlated in some other way to the all atom properties of the sample. In a particular case the second property of the sample is correlated to the total number of nucleons within the object.

In a convenient embodiment, the first data item and the second data item are co-processed numerically to generate a ratio, and this ratio is used to draw inferences about the material content of the sample.

The radiation preferably comprises high-energy radiation such as ionising radiation, for example high-energy electromagnetic radiation such as x-rays and/or gamma rays, and the detection system is adapted correspondingly to detect radiation in this spectrum. The radiation is for example from a broadband source such as a broadband x-ray or gamma-ray source capable of producing broad spectrum emission over a wide range of energies.

In accordance with the method of the invention the radiological technique is used to derive a first data item correlated to the total number of electrons within the sample. This may be done in particular by collecting transmitted intensity information and deriving a measurement of the attenuation by the object to derive a measure of the total number of electrons within a sample.

When an X-ray passes through a medium, there are two main methods in which it can be attenuated:

- At low energy, the Photoelectric effect dominates, in which the photon's energy is transferred to an electron orbiting the atom.
- At higher energies, Compton Scattering takes place, where the photon is scattered off the electrons around the atoms.

Both processes are dependent upon the number of electrons in the path of the X-ray, although not in the same proportion. For example, at low energies for material with an atomic number great than about 10 electron shell effects play a role. Thus the dependence of the absorption on the number of electrons in the beam is also energy dependent.

This invention relates to utilising this phenomenon to obtain a measure of the total number of electrons within a sample (using this X-ray Shadow Technique), and subsequently using this information with an orthogonal technique to collect material identification information.

One embodiment of the X-ray Shadow Technique is to irradiate an entire object with a wide beam of X-rays, and collect the intensity information on an array of detectors.

Different embodiments to gather information on an entire volume range from one single large-size detector, using a movable single detector to scan the entire item, a linear array of a number of pixels with the sample on a belt, through to a two-dimensional array of detectors capturing the entire sample at the same time.

With X-ray information collated over the entire sample through whatever embodiment, the electron count may be calculated from the absorption integrated over all detectors.

As a first approximation, the linear attenuation coefficient ($\mu$) of a material at a given energy $$\mu \propto \rho_e$$

And setting $\beta$ at the constant of proportionality to the electron density $\rho_e$ then $$\mu = \beta \rho_e$$

For the Beer Lambert equation for the output intensity I of a beam at a given energy emerging from a medium of thickness t having incident intensity $I_o$, the transmission T is given by $$T = \frac{I}{I_0} = e^{-\mu t}$$

Taking the logs of both sides, and substituting the earlier equation for the linear attenuation coefficient $$\ln T = -\beta \rho_e t$$

As the X-rays are collected over an area A, we can integrate up over that area $$-\int \beta \rho_e t \, dA = \int \ln T \, dA$$

But $$\int t \, dA = V$$

And $$\rho_e = \frac{N_e}{V}$$

Where V is the volume of the sample under investigation and $N_e$ is the number of electrons within that sample.

$$\therefore N_e = \frac{-1}{\beta} \int \ln T \, dA$$

Hence, if a system is calibrated to obtain β, the number of electrons within the sample can be calculated via a series of transmission measurements.

The method of the invention then uses an orthogonal method to obtain a second data item correlated to another property of the sample, and using this with the measured number of electrons to derive an indication of the material content of the sample. Conveniently for example the second property of the sample is correlated in some other way to the all atom properties of the sample. This second method in its simplest case may be a single measurement, or may be similarly the integration of a number of sub-measurement, which gives a measurement of a total property of the object. These sub-measures may be useful in identifying the non-uniformities within the object when used in correspondence with the individual X-ray path measures.

An example of a simple orthogonal second property of the sample is the total number of nucleons within the object sample. An example of an orthogonal method is to weigh the sample. This effectively gives the total number of nucleons (protons and neutrons) in the sample. As the number of electrons matches the number of protons in an atom, the difference between the nucleon number and electron number will give an indication of the number of neutrons. As displayed in FIG. 1, a standard graph of stable isotopes, the proton to neutron ratio gives a method for discrimination of elements.

An example of a sub-measured orthogonal method is to use a mass sub-measurement system to map the mass profile across the object.

The invention claimed is:

1. A method of radiological examination of an object for identification and detection of a composition of the object, the method comprising the steps of:
    irradiating the object under test with high energy radiation and collecting radiation emergent from the object at a detector system in such manner that emergent radiation intensity data is collected for an entire volume of the object under test;
    numerically processing the radiation intensity data to obtain a first data item correlated to a total number of electrons within the object by performing a calculation derived from radiation absorption integrated over a whole detection area which calculation includes the following steps:
    performing a series of transmission measurements to determine a radiation transmission, T according to the relationship $$T = \frac{I}{I_o}$$

where I is output intensity of a beam of incident intensity $I_0$ emerging from a medium
    integrating over a whole detection area A according to the relationship $$N_e \beta = -\int \ln T \, dA$$

thereby determining a product correlated to the total number of electrons within the object, where β has been set as a constant of proportionality; and
    using the first data item and a second data item to derive an indication of a material content of the object, wherein the second data item is correlated to another property of the object.

2. The method in accordance with claim 1, wherein the first data item and the second data item are co-processed numerically to generate a ratio, and this ratio is used to draw inferences about the material content of the object.

3. The method in accordance with claim 1, wherein the radiation comprises high-energy ionising radiation.

4. The method in accordance with claim 3, wherein the radiation is derived from a broadband x-ray or gamma-ray source.

5. The method in accordance with claim 1, wherein the step of numerically processing the radiation intensity data to obtain a first data item correlated to the total number of electrons within the object by performing a calculation derived from the radiation absorption integrated over a whole detection area which calculation includes the following steps:
    performing a series of transmission measurements to determine a radiation transmission, T according to the relationship $$T = \frac{I}{I_o} = e^{-\mu t}$$

where I is output intensity of a beam of incident intensity $I_0$ at a given energy emerging from a medium of thickness t and linear attenuation coefficient μ;
    integrating over a whole detection area A according to the relationship $$-\int \beta \rho_e t \, dA = \int \ln T \, dA$$

where β has been set as the constant of proportionality to an electron density $\rho_e$;

determining therefrom a total number of electrons within the object, $N_e$, according to the relationship $$N_e = \frac{-1}{\beta} \int \ln T \, dA.$$

6. The method in accordance with claim 1, wherein the radiation comprises at least one of x-rays and gamma-rays.

7. A method of radiological examination of an object for identification and detection of a composition of the object, the method comprising the steps of:

irradiating the object under test with high energy radiation and collecting radiation emergent from the object at a detector system in such manner that emergent radiation intensity data is collected for an entire volume of the object under test;

numerically processing the radiation intensity data to obtain a first data item correlated to a total number of electrons within the object by performing a calculation derived from radiation absorption integrated over a whole detection area which calculation includes the following steps:

performing a series of transmission measurements to determine a radiation transmission, T according to the relationship $$T = \frac{I}{I_o}$$

where I is output intensity of a beam of incident intensity $I_0$ emerging from a medium integrating over a whole detection area A according to the relationship $N_e \beta = -\int \ln T \, dA$ thereby determining a product correlated to the total number of electrons within the object, where β has been set as a constant of proportionality;

using the first data item and a second data item to derive an indication of a material content of the object; and wherein the second data item is selected to be correlated to all atom properties of the object.

8. The method in accordance with claim 7, wherein the radiation comprises at least one of x-rays and gamma-rays.

9. The method in accordance with claim 7, wherein the second data item is correlated to a total number of nucleons within the object.

10. The method in accordance with claim 7, wherein the first data item and the second data item are co-processed numerically to generate a ratio, and this ratio is used to draw inferences about the material content of the object.

11. The method in accordance with claim 7, wherein the radiation comprises high-energy ionising radiation.

12. A method of radiological examination of an object for identification and detection of a composition of the object, the method comprising the steps of:

irradiating the object under test with high energy radiation and collecting radiation emergent from the object at a detector system in such manner that emergent radiation intensity data is collected for an entire volume of the object under test;

numerically processing the radiation intensity data to obtain a first data item correlated to a total number of electrons within the object by performing a calculation derived from radiation absorption integrated over a whole detection area which calculation includes the following steps:

performing a series of transmission measurements to determine a radiation transmission, T according to the relationship $$T = \frac{I}{I_o}$$

where I is output intensity of a beam of incident intensity $I_0$ emerging from a medium integrating over a whole detection area A according to the relationship $N_e \beta = -\int \ln T \, dA$ thereby determining a product correlated to the total number of electrons within the object, where β has been set as a constant of proportionality;

using the first data item and a second data item to derive an indication of a material content of the object; and wherein the second data item is selected as one that can be co-processed with a measurement of the total number of electrons to draw inferences about the material content without requiring measurement of the volume.

13. The method in accordance with claim 12, wherein the second data item is selected as one that can be processed numerically with the first data item correlated to the total number of electrons within the object so that the respective volume contributions to the data items can be cancelled out.

14. The method in accordance with claim 13, wherein both data items are derived as total numbers integrated over the volume under investigation, so that knowledge of the volume of the object is no longer required.

15. The method in accordance with claim 12, wherein the radiation comprises at least one of x-rays and gamma-rays.

16. The method in accordance with claim 12, wherein the second data item is correlated to a total number of nucleons within the object.

17. The method in accordance with claim 12, wherein the first data item and the second data item are co-processed numerically to generate a ratio, and this ratio is used to draw inferences about the material content of the object.

18. The method in accordance with claim 12, wherein the radiation comprises high-energy ionising radiation.

* * * * *